United States Patent [19]

Sasse et al.

[11] Patent Number: 5,502,069
[45] Date of Patent: Mar. 26, 1996

[54] 1-THIOCARBAMOYL-5-HYDROXY-PYRAZOLES AS MICROBICIDES

[75] Inventors: Klaus Sasse, Bergisch Gladbach; Peter Wachtler, Cologne; Georg-Wilhelm Ludwig; Wilfried Paulus, both of Krefeld, all of Germany

[73] Assignee: Bayer Aktiengesellschaft, Leverkusen, Germany

[21] Appl. No.: 302,076

[22] Filed: Sep. 7, 1994

Related U.S. Application Data

[63] Continuation of Ser. No. 84,781, Jun. 29, 1993, abandoned, which is a continuation of Ser. No. 884,679, May 18, 1992, abandoned.

[30] Foreign Application Priority Data

May 28, 1991 [DE] Germany ............ 41 17 385.6

[51] Int. Cl.⁶ .................................................. A01N 43/56
[52] U.S. Cl. ........................................ 514/404; 548/369.7
[58] Field of Search ............................ 548/369.7; 514/404

[56] References Cited

PUBLICATIONS

Nishimura, Chem Abstracts, vol. 92 (1980) No. 76497n.
Nishimura, Chem Abstracts, vol. 92 (1980) No. 53377j.
Miyamoto, Chem Abstracts, vol. 105 (1986) No. 185732t.
Nippon Noyaku Gakkaishi, 1986 11(2), 205–12 (Eng).
Patent Abstracts of Japan, vol. 3, No. 138 (C–64), Nov. 16, 1979, p. 161.

*Primary Examiner*—Robert W. Ramsuer
*Attorney, Agent, or Firm*—Sprung Horn Kramer & Woods

[57] ABSTRACT

1-Thiocarbamoyl-5-hydroxy-pyrazoles have a microbicidal action and are therefore suitable for use for the preservation of materials. Since, in contrast to other microbicides, they are ecologically acceptable and do not discolour plastics, paints and paint films, they are particularly recommended for use in these substances.

2 Claims, No Drawings

1-THIOCARBAMOYL-5-HYDROXY-PYRAZOLES AS MICROBICIDES

This application is a continuation, of application Ser. No. 084,781, filed Jun. 29, 1993.

The invention relates to the use of 1-thiocarbamoyl-5-hydroxy-pyrazoles of the formula

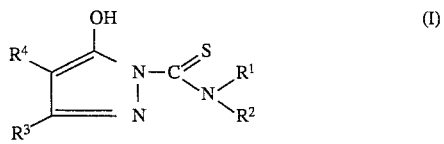

wherein the substituents have the meaning given in the main claim, as microbicides for the preservation of industrial materials, new 4-substituted 1-thiocarbamoyl-hydroxy-pyrazoles and a process for their preparation by condensation of α-formyl-carboxylic acid esters or amides or of β-ketoacetic acid esters or amides with thiosemicarbazides.

1-Hetaryl-4-aryl-pyrazolin-5-ones, for example 1-[pyri(mi)d-2-yl]-4-phenyl-pyrazolin-5-ones, and microbicidal properties thereof are known from U.S. Pat. No. 4,663,327. However, since the compounds are coloured and lead to discolourations when incorporated into industrial materials, for example paints and plastics, they cannot be used for the preservation of materials, in spite of their good microbicidal properties.

Organoarsenic compounds are to date still being used for fungicidal treatment of plastics, although the replacement of these compounds and also of the organo-mercury compounds still used in paints is highly desirable for ecotoxicological reasons. However, no ecotoxicologically more favourable compounds which fulfil the high requirements which must be imposed on microbicides which can be used for the microbicidal treatment of plastics have as yet been found. Such microbicides must in fact also have a high heat resistance, in addition to a good microbicidal activity, and moreover should not impair the properties of the plastics, for example not discolour these. This last requirement also applies to microbicides which are to be employed in paints.

It has been found, surprisingly, that 1-thiocarbamoyl-5-hydroxy-pyrazoles do not have the disadvantages of the prior art and fulfil all the requirements imposed on such active compounds. Although they are ecotoxicologically acceptable, they achieve the action of the undesirable organoarsenic and -mercury compounds. They have the necessary heat stability and do not adversely impair the properties, such as colour and elasticity, of the plastics, paints and paint films treated with them.

The invention thus relates to the use of compounds of the formula I, wherein $R^1$ us $R^2$ independently of one another denote hydrogen or optionally substituted alkyl, $R^3$ denotes hydrogen or optionally substituted alkyl, alkenyl, alkinyl, cycloalkyl, alkoxycarbonyl, aralkyl or aryl, $R^4$ denotes hydrogen or optionally substituted alkyl, alkenyl, alkinyl, cycloalkyl, alkoxy, alkylthio, aralkyl, aralkoxy, aralkylthio, aryl, aryloxy, arylthio, alkoxycarbonyl, alkoxycarbonylmethyl or aminocarbonyl, or $R^3$ and $R^4$ together denote a 1,ω-$C_3$-$C_6$-alk(en)ylene radical, as microbicides for the preservation of industrial materials.

Preferred meanings for the substituents $R^1$ to $R^4$ are explained below:

Alkyl represents straight-chain or branched alkyl having preferably 1 to 12 C atoms, such as methyl, ethyl, n- and i-propyl, n-, sec.-, i- and tert.-butyl, n-, i- and tert.-phenyl, n-hexyl, i-octyl, i-nonyl, n-decyl and n-dodecyl. These alkyl groups can be substituted by 1 to 3 halogen atoms, preferably chlorine and/or fluorine, or by a $C_1$-$C_6$-alkoxycarbonyl group. Substituted alkyl groups accordingly include, for example, mono-, di- and trifluoromethyl, monochlorodifluoromethyl and methoxy- and ethoxycarbonylmethyl.

The term alkoxy includes straight-chain and branched alkoxy having preferably 1 to 12 C atoms, such as, for example, methoxy, ethoxy, n-and i-propoxy, n-, i-, sec.- and tert.-butoxy and hexoxy.

Alkenyl denotes straight-chain or branched alkenyl having preferably 2 to 6 C atoms, such as, for example, vinyl and allyl.

Alkinyl represents straight-chain or branched alkinyl having preferably 2 to 6 C atoms, such as, for example, ethinyl, propinyl and 3,3-dimethylpropinyl; preferred substituted alkinyl groups are, in particular, the iodine-substituted alkinyls, such as, for example, 1-iodo-propinyl.

Cycloalkyl groups include cycloalkyl having preferably 5 to 7 C atoms, such as, for example, cyclohexyl; preferred substituted cycloalkyl groups include cycloalkyl which is substituted by 1 to 3 $C_1$-$C_4$-alkyl groups or 1 to 3 halogen atoms, such as chlorine and/or fluorine, such as, for example, methylcyclohexyl, dimethylcyclohexyl, 1,3,3,-trimethylcyclohexyl and 3-chlorocyclohexyl.

Alkoxycarbonyl represents straight-chain or branched alkoxycarbonyl having preferably 1 to 6 C atoms in the alkoxy radical, such as, for example, methoxycarbonyl, ethoxycarbonyl, n- and i-propoxycarbonyl, n-, i-, sec.- and tert.-butoxycarbonyl and hexoxycarbonyl. Analogous comments apply to the alkoxycarbonylmethyl groups.

Aralkyl preferably contains 1 to 6, in particular 1 to 4, C atoms in the straight-chain or branched alkyl part and preferably phenyl or naphthyl as the aryl part. Examples of such aralkyl groups include benzyl, α-methylbenzyl, α,α-dimethylbenzyl, 2-phenethyl and α- and β-naphthylmethyl. These aralkyl radicals can carry 1 to 3 substituents from the series comprising halogen (in particular chlorine and/or fluorine), nitro, cyano, optionally halogenated $C_1$-$C_4$-alkyl or -alkoxy, such as, for example, methyl, ethyl, trifluoromethyl, difluorochloromethyl, difluoromethyl, trichloromethyl, methoxy, ethoxy, trifluoromethoxy, difluorochloromethoxy and difluoromethoxy, and optionally halogenated $C_1$-$C_4$-alkylmercapto, such as, for example, methylmercapto, trifluoromethylmercapto and difluorochloromethylmercapto.

The term aryl is to be understood as meaning unsubstituted or substituted aryl having preferably 6 to 10 C atoms in the aryl part. Preferred examples include phenyl and naphthyl. The aryl groups can carry 1 to 3 substituents from the series comprising halogen (in particular chlorine and/or fluorine), $C_1$-$C_4$-alkyl or -alkoxy, halogeno-$C_1$-$C_2$-alkyl, (such as trifluoromethyl and difluoromethyl), cyano, nitro or amino.

The term alkoxy is to be understood as meaning straight-chain and branched alkoxy having preferably 1 to 6, in particular 1 to 4, C atoms. Preferred examples include methoxy, ethoxy, n- and i-propoxy, n-, i-, sec.- and tert.-butoxy and hexoxy.

Alkylthio represents straight-chain or branched alkylthio having preferably 1 to 6 C atoms. Preferred examples include methylthio, ethylthio, n- and i-propylthio, n-, i-, sec.- and tert.-butylthio and n-pentylthio and its isomers, such as 1-, 2- and 3-methyl-butylthio. The alkylthio groups can be substituted by 1 to 3 halogen atoms (preferably chlorine and/or fluorine); preferred examples of these are di- and trifluoromethylthio and difluorochloromethylthio.

Aralkoxy preferably contains 1 to 6 C atoms in the straight-chain or branched alkyl part and preferably phenyl as the aryl part. Preferred examples are benzyloxy and phenetyloxy. The aralkoxy groups can be substituted by 1 to 3 halogen atoms (preferably chlorine and/or fluorine) or by a $C_1$-$C_4$-alkyl group.

Aralkylthio preferably contains 1 to 6 C atoms in the straight-chain or branched alkyl part and preferably phenyl as the aryl part. A preferred example is benzylthio. The aralkylthio groups can be substituted by 1 to 3 halogen atoms (preferably chlorine and/or fluorine) or by a $C_1$-$C_4$-alkyl group.

Aryloxy preferably contains 1 to 10 C atoms in the aryl part. Preferred examples are phenoxy and naphthoxy. The aryloxy groups can carry through 1 to 3 substituents from the series comprising halogen (preferably chlorine and/or fluorine), $C_1$-$C_4$-alkyl, halogen-$C_1$-$C_2$-alkyl (such as di- and trifluoromethyl), cyano, nitro or amino.

Arylthio preferably contains 6 to 10 C atoms in the aryl part 1. Preferred examples are phenylthio and naphthylthio. The arylthio groups can carry the substituents listed under "aryloxy".

The term aminocarbonyl includes, for example, unsubstituted aminocarbonyl, N-methylaminocarbonyl and N,N-dimethyaminocarbonyl.

Preferred example of 1, ω-$C_3$-$C_6$-alk(en)ylene radicals include 1,3-propylene, 1,4-butylene and 1,4-butadien-(1,3)-ylene.

Compounds of the formula (I), wherein $R^1$ denotes hydrogen or optionally substituted alkyl, aralkyl or aryl, $R^2$ denotes hydrogen, $R^3$ denotes hydrogen or optionally substituted alkyl or aryl and $R^4$ denotes hydrogen or optionally substituted alkyl, cycloalkyl, aralkyl, alkoxycarbonyl or aryl, are preferred.

Compounds of the formula I, wherein $R^1$-$R^3$ denote hydrogen and $R^4$ denotes hydrogen or optionally substituted alkyl, aralkyl or aryl, are particularly preferred.

The most preferred compounds correspond to the formula I, wherein $R^1$-$R^3$ denote hydrogen and $R^4$ denotes $C_1$-$C_6$-alkyl, benzyl or phenyl.

Typical representatives of the compounds I to be used according to the invention are listed in the examples.

The compounds I to be used according to the invention can also be present in their tautomeric pyrazol-5-one form.

The compounds I to be used according to the invention and processes for their preparation are known in some cases. 3-mono- and 3,4-di-substituted 1-thiocarbamoyl-5-hydroxy-pyrazoles which have an action against plant diseases are thus described in the published Japanese Patent Applications 79/115,374 and 79/119,031. In particular, they are said to have a fungicidal action; compare also J. Pesticide, Sci. 11, 205–212 (1986).

4-Mono- and 3,4-di-substituted 1-thiocarbamoyl-5-hydroxypyrazoles having an antihistamine action are known from Arch. Pharm. (Weinheim) 316, 2–6 (1983) and Sci. Pharm. 51 (2), 167–172 (1982).

Where the compounds are still new they can be prepared by processes analogous to the known preparation processes.

An α-formyl-carboxylic acid ester or an α-formyl-carboxylic acid amide or a β-ketoacetic acid ester or a β-ketoacetic acid amide is usually reacted with a thiosemicarbazide. This condensation reaction proceeds according to the following equation (demonstrated using ethyl β-ketoacetate as the β-diketo starting substance):

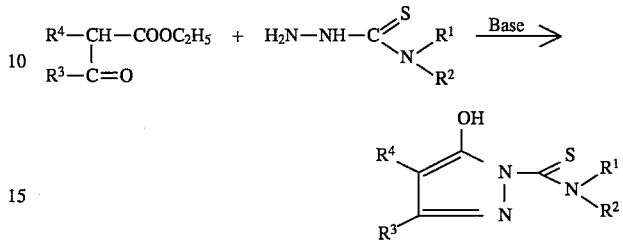

The substituents $R^1$ to $R^4$ in the above equation have the meanings given above for the compounds of the formula I.

0.8 to 1.0 mol of thiosemicarbazide is preferably added per mol of α-formyl-carboxylic acid ester derivative or per mol of β-diketo compound.

Bases, such as sodium hydroxide, potassium hydroxide or potassium tert.-butylate, are advantageously added to facilitate the cyclisation reaction. The base is preferably added in an amount which is approximately equivalent to that of the β-formylcarboxylic acid ester derivative of the α-diketo compound.

If appropriate, the condensation can be carried out in the presence of a solvent; solvents which have proved suitable are, above all, alcohols, such as ethanol, or aromatic hydrocarbons, such as toluene.

The condensation reaction can be carried out within a relatively wide temperature range. The thiosemicarbazone formation which first proceeds can be carried out at temperatures of from 20° to 110° C., preferably between 60° and 90° C. The cyclocondensation reaction which proceeds after the addition of the base can be carried out at temperatures of from 20° to 100°, preferably 20° to 40° C. Since the addition of the base proceeds exothermically in some cases, cooling may be necessary during this reaction step.

The 1-thiocarbamoyl-hydroxy-pyrazoles can be isolated from the reaction mixtures by known methods. A procedure is in general followed in which the reaction mixtures are freed from the solvent and the residue is treated with aqueous hydrochloric acid. The pyrazoles obtained by this procedure are separated off by filtration with suction. However, it is also possible for the reaction mixture to be poured directly into a large excess of dilute hydrochloric acid and for the pyrazoles which separated out as a precipitate to be filtered off.

The starting compounds required for the preparation of the compounds I to be used according to the invention, that is to say the α-formyl-carboxylic acid esters or amides and the β-ketoacetic acid esters or amides which are optionally substituted in the α-position and the optionally substituted thiosemicarbazides, are either known compounds or can be prepared analogously to known compounds by processes which have already been described.

As already mentioned above, some compounds I to be used according to the invention are new. The invention thus furthermore relates to compounds of the formula

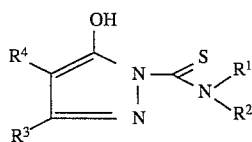

wherein $R^1$ and $R^2$ have the meaning given in the main claim, $R^3$ represents hydrogen and $R^4$ represents optionally substituted $C_6$-$C_8$-alkyl, optionally substituted aryl having preferably 6 to 10 C atoms, excluding phenyl and 4-chlorophenyl as substituents $R^4$, or optionally substituted aralkyl having preferably 1 to 6, in particular 1 to 4, C atoms in the straight-chain or branched alkyl part and 6 to 10 C atoms in the aryl part, with the exception of unsubstituted benzyl.

The terms "alkyl", "aryl" and "aralkyl" used for $R^4$ in formula (II) and their substituents which are optionally present correspond to the meanings given above for "alkyl", "aryl" and "aralkyl" and their substituents optionally present in the formula (I), in the context of the limitations of the formula (II).

The invention furthermore relates to a process for the preparation of the compound II, in which compounds of the formulae

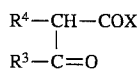

and

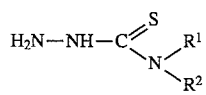

wherein $R^1$ to $R^4$ have the meaning given for formula II and

X represents $C_1$-$C_4$-alkoxy, phenoxy or amino, are reacted in a manner which is known per se.

The materials which can be preserved by the compounds I to be used according to the invention are non-living materials which have been prepared for use in industry. Industrial materials which are to be preserved by the active compounds to be used according to the invention against microbial change or destruction can be, for example, adhesives, sizes, paper and card, textiles, leather, wood, paints, plastics and articles made of plastic, cooling lubricants and other materials which may be attacked or decomposed by microorganisms. In the context of the materials to be preserved, there may also be mentioned components of production plants, for example cooling water circulations, the functioning of which may be impaired by multiplication of microorganisms. In the context of the present invention, industrial materials are preferably understood to mean paints, plastics, articles made of plastic and wood.

Microorganisms which can cause degradation of or a change in industrial materials include, for example, bacteria, fungi, yeasts, algae and slime organisms. The active compounds to be used according to the invention preferably act against fungi, in particular against moulds and against fungi which permanently discolour wood and wood-destroying fungi;

that is to say, for example, microorganisms of the following genera:

Alternaria, such as *Alternaria tenuis*, Aspergillus, such as *Aspergillus niger*, Chaetomium, such as *Chaetomium globosum*, Coniophora, such as *Coniophora puteana*, Lentinus, such as *Lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pityophila*, Trichoderma, such as Trichoderma viride, Escherichia, such as *Escherichia coli*, Pseudomonas, such as *Pseudomonas aeruginosa* and Staphylococcus, such as *Staphylococcus aureus*.

The active compounds to be used according to the invention can be converted into the customary formulations, such as solutions, emulsions, suspensions, powders, pastes and granules, depending on the field of use.

These can be prepared in a manner which is known per se, for example by mixing the active compounds with an extender, which consists of a liquid solvent and/or solid carriers, if appropriate using surface-active agents, such as emulsifiers and/or dispersing agents, it being possible, if appropriate, in the case where water is used as the extender, for organic solvents, such as alcohols, to be used as auxiliaries.

Liquid solvents for the active compounds can be, for example, water, alcohols, such as lower aliphatic alcohols, preferably ethanol or isopropanol, or benzyl alcohol, ketones, such as acetone or methyl ethyl ketone, liquid hydrocarbons, such as benzine fractions, and halogenated hydrocarbons, such as 1,2-dichloroethane.

The microbicidal agents used for the preservation of industrial materials in general contain the active compounds in an amount of from 1 to 100% by weight, preferably from 10 to 90% by weight.

The use concentrations of the active compounds to be used according to the invention depend on the nature and occurrence of the microorganisms to be combated and on the composition of the material to be preserved. The optimum amount employed can be determined by test series. The use concentrations are in general in the range from 0.001 to 5% by weight, preferably from 0.05 to 1.0% by weight, based on the material to be preserved.

The active compounds to be used according to the invention can also be used as a mixture with other known active compounds. The following active compounds may be mentioned as examples: benzyl alcohol mono(poly)hemiformal and other compounds which split off formaldehyde, benzimidazolyl methylcarbamates, tetramethylthiuram disulphide, zinc salts of dialkyldithiocarbamates, 2,4,5,6-tetrachloroisophthalonitrile, thiazolylbenzimidazole, mercaptobenzothiazole, 2-thiocyanatomethylthiobenzothiazole, methylene bisthiocyanate, phenol derivatives, such as 2-phenylphenol, (2,240-dihydroxy-5,5'-dichloro)-diphenylmethane and 3-methyl-4-chloro-phenol, organotin compounds, N-trihalogenomethylthio compounds, such as folpet, fluorfolpet and dichlofluanid, azole fungicides, such as triadimefon, triadimenol, bitertanol, tebuconazole and propiconazole, and iodopropargyl compounds, such as IPBC.

Mixtures of the compounds I to be used according to the invention with other known insecticides can also be employed. Preferred examples of such other insecticides include phosphoric acid esters, such as azinphos-ethyl, azinphos-methyl, 1-(4-chlorophenyl)-4-(O-ethyl, S-propyl)phosphoryloxypyrazole (TIA-230), chlorpyrifos, coumaphos, demeton, demeton-S-methyl, diazinon, dichlorvos, dimethoate, ethoprophos, etrimfos, fenitrothion, fenthion, heptenophos, parathion, parathion-methyl, phosalone, pirimphos-ethyl, pirimiphos-methyl, profenofos, prothiofos, sulprofos, triazophos and trichlorphon;

carbamates, such as aldicarb, bendiocarb, BPMC (2-(1-methylpropyl)phenyl methylcarbamate), butocarboxime, butoxycarboxime, carbaryl, carbofuran, carbosulfan, cloethocarb, isoprocarb, methomyl, oxamyl, pirimicarb, promecarb, propoxur and thiodicarb; and pyrethroids, such as allethrin, alphamethrin, bioresmethrin, byfenthrin (FMC 54 800), cycloprothrin, cyfluthrin, cyhalothrin, cypermethrin, deltamethrin, alpha-cyano-3-phenyl-2-methylbenzyl 2,2-dimethyl-3-(2-chloro-2-trifluoromethylvinyl) cyclopropanecarboxylate, fenpropathrin, fenfluthrin, fenvalerate, flucythrinate, flumethrin, fluvalinate, permethrin and resmethrin.

The percentage data which occur in the following examples relate to the weight.

EXAMPLES

Example 1–6 (3-monosubstituted compounds)

4.6 g (0.05 mol) of thiosemicarbazide and 7.9 g (0,.05 mol) of ethylbutyrylacetate are kept at the reflux temperature together with 100 ml of ethanol for 3 hours. The mixture is then allowed to cool to room temperature and 5.9 g (0.05 mol, 97 % pure) of potassium tert.-burylate are added in portions, while stirring, and stirring is then continued at room temperature for 4 hours. The contents of the flask are subsequently stirred into a mixture of 800 ml of water/50 ml of concentrated HCl and the precipitate which has separated out is filtered off with suction. After thorough washing with water, the moist product is left in a drying cabinet (50 mbar/60° C.) until it reaches constant weight.

Yield: 6.9 g (74.5% of theory)

Melting point: 160°–161° C. colourless solid.

The 1-thiocarbamoyl-5-hydroxy-pyrazoles substituted in the 3-position and listed in the following Table 1 can be obtained in the same manner from the corresponding acylacetic acid ethyl esters.

The pyrazoles obtained are characterised by melting point determination.

TABLE 1

| Examples | $R^3$ | $R^4$ | $R^1, R^2$ | Melting point |
| --- | --- | --- | --- | --- |
| 1 | $C_3H_7$ | H | H | 160–161° C. |
| 2 | $CH_3$ | H | H | 178° C. |
| 3 | $C_2H_5$ | H | H | 154–158° C. |
| 4 | $C_6H_{13}$ | H | H | 142–143° C. |
| 5 | $C_8H_{17}$ | H | H | 134–135° C. |
| 6 | $C_{10}H_{21}$ | H | H | 154° C. |

Examples 7–14 (3,4-disubstituted compounds)

A mixture of 3.9 g (0.025 mol) of ethyl 2-ethyl-acetoacetate, 2.3 g (0.025 mol) of thiosemicarbazide and 100 ml of ethanol is kept at the reflux temperature for 3 hours, while stirring. The reaction mixture is subsequently cooled to 20° C., and 2.9 g (0.025 mol; 97% pure) of potassium tert.-butylate are added in portions, while stirring. The resulting suspension is then stirred at 20°–30° C. for 3 hours and subsequently stirred into dilute hydrochloric acid (500 ml of water/20 ml of concentrated HCl ), and the precipitate is filtered off with, suction. The product is washed thoroughly with water and dried to constant weight under the influence of heat.

Yield: 2.9 g ( 82.5% of theory)

Melting point: 163° C. The 3,4-disubstituted 1-thiocarbamoyl-5-hydroxypyrazoles listed in the following Table 2 can be obtained in the same manner from the corresponding α-substituted β-keto esters.

TABLE 2

| Examples | $R^3$ | $R^4$ | $R^1, R^2$ | Melting point |
| --- | --- | --- | --- | --- |
| 8 | $CH_3$ | $C_4H_9$ | H | 139° C. |
| 9 | $CH_3$ | $C_7H_{15}$ | H | 124° C. |
| 10 | $CH_3$ | $C_{12}H_{25}$ | H | 112° C. |
| 11 | $CH_3$ | $(CH_3)_2C=CH-CH_2$ | H | 148° C. |
| 12 | $CH_3$ | $C_6H_5-CH(CH_3)-$ | H | 143° C. |
| 13 | $C_2H_5$ | $CH_3$ | H | 152–153° C. |
| 14 | $R^3 + R^4 =$ | $-(CH_2)_4-$ | H | 179–180° C. |

Examples 15–42

10.3 g (0.06 mol) of ethyl α-formyl-hexanoate and 5.5 g (0.06 mol ) of thiosemicarbazide are initially introduced into 200 ml of ethanol and the mixture is stirred at 80° C. for 3 hours.

The mixture is then brought to room temperature, 6.9 g of potassium tert.-butylate are added, while stirring, and stirring is then continued at room temperature for 4 hours. The contents of the flask are subsequently stirred into a mixture of 800 ml of water and 50 ml of concentrated hydrochloric acid and the resulting precipitate is filtered off with suction. After thorough washing with water, the product is left in a drying cabinet until it reaches constant weight. The compound can be purified by recrystallisation from ethanol.

Yield: 9.4 g (80.3% of theory) Melting point: 139°–141° C.

The 4-substituted 1-thiocarbamoyl-5-hydroxypyrazoles listed in the following Table 3 can be obtained in the same manner from the corresponding α-formyl-carboxylic acid esters.

TABLE 3

| Example | $R^4$ | $R^1, R^2, R^3$ | Melting point |
| --- | --- | --- | --- |
| 16 | $CH_3-$ | H | 164–165° C. |
| 17 | $C_2H_5-$ | H | 144–145° C. |
| 18 | $C_6H_{13}-$ | H | 136–137° C. |
| 19 | $C_{10}H_{21}-$ | H | 128° C. |
| 20 | $(CH_3)_2CH-CH_2-$ | H | 128–131° C. |
| 21 | $(CH_3)_2CH-CH_2-CH_2-$ | H | 153–154° C. |

TABLE 3-continued
| Example | R⁴ | R¹, R², R³ | Melting point |
|---|---|---|---|
| 22 | COOC₂H₅ | H | 178° C. |
| 23 | CH₂=CH—CH₂— | H | 134–135° C. |
| 24 | CH₃O— | H | 149–150° C. |
| 25 | 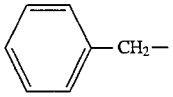 | H | 161–162° C. |
| 26 | 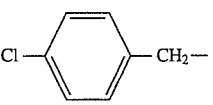 | H | 166–167° C. |
| 27 | 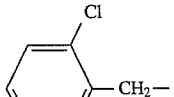 | H | 152–154° C. |
| 28 | 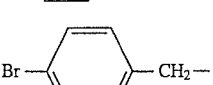 | H | 170–171° C. |
| 29 | 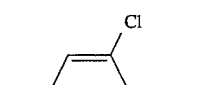 | H | 186° C. |
| 30 | 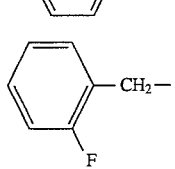 | H | 170–172° C. |
| 31 | 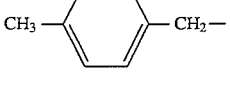 | H | 186° C. |
| 32 | 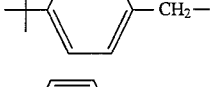 | H | >200° C. |
| 33 | 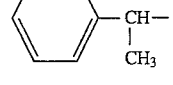 | H | 161–163° C. |
| 34 | 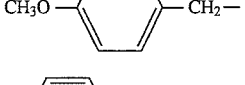 | H | 160° C. |
| 35 | 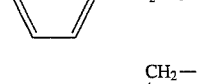 | H | 177–178° C. |
| 36 | 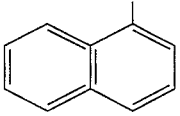 | H | 169–170° C. |
| 37 | 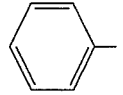 | H | 175° C. |
| 38 | 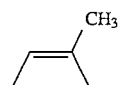 | H | 200° C. (decomposition) |
| 39 | 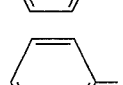 | H | 157–158° C. |
| 40 | 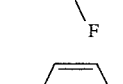 | H | 231–232° C. |
| 41 |  | H | 231–233° C. |
| 42 | 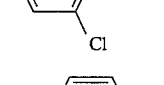 | H | 240–243° C. |
| 43 | 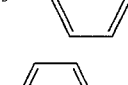 | H | 173° C. |
| 44 | 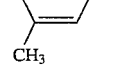 | H | 163° C. |
| 45 | 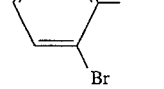 | H | 263–264° C. |
| 46 | 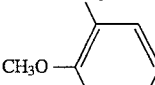 | H | 174–175° C. |
| 47 | 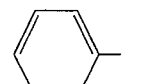 | H | 284–286° C. |
| 48 | 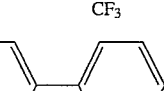 | H | 174–176° C. |

TABLE 3-continued

| Example | R⁴ | R¹, R², R³ | Melting point |
|---|---|---|---|
| 49 | 2-naphthyl | H | 236–237° C. |
| 50 | 2-methoxyphenyl (OCH₃) | H | 150° C. |
| 51 | 3-methoxyphenyl (H₃CO) | H | 162–163° C. |
| 52 | 3,4-dimethoxyphenyl (CH₃, O-CH₃) | H | 167° C. |
| 53 | 4-bromophenyl (Br) | H | 171–172° C. |
| 54 | 4-fluorophenyl (F) | H | 174–175° C. |
| 55 | 4-fluoro-2-methylphenyl (F, CH₃) | H | 171–172° C. |
| 56 | 3-chlorophenyl (Cl) | H | 168–169° C. |
| 57 | 3,4-dichlorophenyl (Cl, Cl) | H | 171–173° C. |
| 58 | 3,4-dimethylphenyl (CH₃, CH₃) | H | 178–179° C. |
| 59 | 3-phenoxyphenyl | H | 148–149° C. |
| 60 | 3-(ethoxycarbonyl)phenyl (H₅C₂O–C(=O)–) | H | 165–167° C. |
| 61 | cyclohexyl | H | 157–158° C. |
| 62 | (4-chlorophenyl)thio (Cl–C₆H₄–S–) | H | 207–208° C. |
| 63 | phenylthio (C₆H₅–S–) | H | 231–214° C. |
| 64 | phenoxy (C₆H₅–O–) | H | 207° C. |

Use examples

Example A

To demonstrate the activity against fungi, the minimum inhibitory concentrations (MIC) of the compounds to be used according to the invention were determined:

Active compounds to be used according to the invention are added in concentrations of 0.1 mg/l to 5000 mg/l to an agar prepared from beer wort and peptone. After solidification of the agar, it is contaminated with pure cultures of the test organisms listed in the table. After storage at 28° C. and 60 to 70% relative atmospheric humidity for 2 weeks, the MIC is determined. The MIC is the lowest concentration of active compound at which no growth at all by the species of microbe used takes place; it is shown in the following Table 4.

TABLE 4

MIC values [mg/l] of various 1-thiocarbamoyl-5-hydroxy-pyrazoles on fungi

| Test organisms | 1-Thiocarbamoyl-5-hydroxy-pyrazoles according to Example | | | | | | | |
|---|---|---|---|---|---|---|---|---|
| | 15 | 21 | 23 | 25 | 26 | 27 | 33 | 34 |
| Alternaria tenuis | 5 | 10 | 50 | 50 | 50 | 50 | 50 | 50 |
| Aspergillus niger | 50 | 20 | 75 | 100 | 50 | 75 | 50 | 100 |
| Aureobasidium pullulans | 5 | 15 | 15 | 20 | 20 | 15 | 50 | 50 |
| Chaetomium globosum | 10 | <10 | 20 | 20 | 15 | 20 | 75 | 20 |
| Cladosporium herbarum | 20 | 20 | 75 | 50 | 50 | 50 | 50 | 50 |
| Lentinus tigrinus | 20 | <10 | 50 | 50 | <10 | 20 | 20 | 20 |
| Penicillium brevicaule | 20 | 15 | 20 | 50 | 15 | 75 | 75 | 75 |
| Sclerophoma pityophila | 15 | 15 | 75 | 50 | 100 | 35 | 35 | 50 |

TABLE 4-continued

MIC values [mg/l] of various
1-thiocarbamoyl-5-hydroxy-pyrazoles on fungi

| Test organisms | 1-Thiocarbamoyl-5-hydroxy-pyrazoles according to Example | | | | | | | |
|---|---|---|---|---|---|---|---|---|
| | 15 | 21 | 23 | 25 | 26 | 27 | 33 | 34 |
| Trichoderma viride | 20 | 35 | 50 | 75 | 50 | 35 | 50 | 100 |

Example B (fungicidal action in paints)

The fungicidal action in paints is determined by testing the resistance of paint films obtained with the paints to mould.

The test is carried out in accordance with Report 219 of the Defense Standards Laboratories Maribyrnong/Australia as follows:

The paint to be tested is brushed onto both sides of a suitable substrate.

To obtain results close to those in practice, some of the test specimens are treated with a hot stream of fresh air before the test for resistance to moulds (7 days; 40° C.).

The test specimens prepared in this way are placed on an agar nutrient medium. The test specimen and nutrient medium are contaminated with fungus spores. After storage at 29°±1° C. and 80 to 90% relative atmospheric humidity for 1 to 3 weeks, the specimens are inspected. The paint film is permanently mould-resistant if the test specimen remains free from fungus or reveals at most a slight attack on the edge.

Fungus spores of the following nine moulds, which are known as destroyers of paint films or are often encountered on paint films, are used for the contamination:

1. *Alternaria tenuis*
2. *Aspergillus flavus*
3. *Aspergillus niger*
4. *Aspergillus ustus*
5. *Cladosporium herbarum*
6. *Paecilomyces variotii*
7. *Penicillium citrinum*
8. *Aureobasidium pullulans*
9. *Stachybotrys atra Corda*

0 to 2% by weight, based on the total solids content of the paint, of the compound to be tested for its fungicidal activity were incorporated into samples of a commercially available dispersion paint based on polyvinyl acetate. In this test, the samples which contained only 0.3% by weight, based on the total solids content of the paint, of the 1-thiocarbamoyl-4-n-butyl-5-hydroxy-pyrazole described in Example 15 already gave colourless permanently mould-resistant paint films.

We claim:

1. A process for the preservation of an industrial material which comprises applying to said material a microbicidally effective amount of a compound selected from the group consisting of:

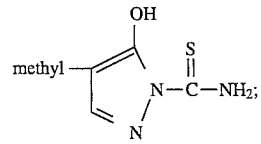

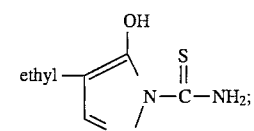

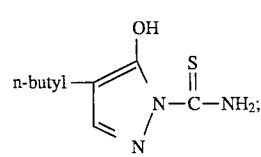

and

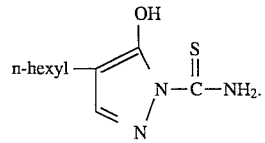

2. A compound of the formula:

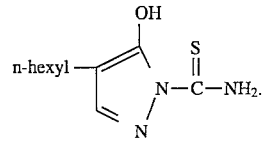

* * * * *